(12) United States Patent
Schäfer et al.

(10) Patent No.: US 10,617,811 B2
(45) Date of Patent: Apr. 14, 2020

(54) PERISTALTIC PUMP HAVING ROTATORY PLAY

(71) Applicant: B. BRAUN AVITUM AG, Melsungen (DE)

(72) Inventors: Oliver Schäfer, Neuenstein (DE); Andreas Iske, Söhrewald (DE)

(73) Assignee: B. Braun Avitum AG, Melsungen (DE)

( * ) Notice: Subject to any disclaimer, the term of this patent is extended or adjusted under 35 U.S.C. 154(b) by 334 days.

(21) Appl. No.: 15/666,888

(22) Filed: Aug. 2, 2017

(65) Prior Publication Data

US 2018/0043074 A1 Feb. 15, 2018

(30) Foreign Application Priority Data

Aug. 11, 2016 (DE) .................. 10 2016 114 959

(51) Int. Cl.
*A61M 1/26* (2006.01)
*A61M 1/10* (2006.01)
*F04B 43/12* (2006.01)

(52) U.S. Cl.
CPC .......... *A61M 1/267* (2014.02); *A61M 1/1039* (2014.02); *F04B 43/1276* (2013.01)

(58) Field of Classification Search
CPC . F04B 43/1276; F04B 43/1253; A61M 1/267; A61M 1/1039; A61M 1/1043; A61M 1/10006
USPC ............................................. 464/160; 74/160
See application file for complete search history.

(56) References Cited

U.S. PATENT DOCUMENTS

| | | | | |
|---|---|---|---|---|
| 2,348,071 A | * | 5/1944 | McC Johnstone | ........ F16D 1/02 403/305 |
| 3,737,256 A | | 6/1973 | De Vries | |
| 4,432,707 A | | 2/1984 | Anderson et al. | |
| 4,527,323 A | | 7/1985 | Dawson | |
| 4,551,115 A | * | 11/1985 | Ferguson | .................. F16D 3/12 464/160 |

(Continued)

FOREIGN PATENT DOCUMENTS

| | | |
|---|---|---|
| CN | 1560474 A | 1/2005 |
| CN | 203598285 U | 5/2014 |

(Continued)

OTHER PUBLICATIONS

Extended European Search Report for European Application No. 17184562.1, dated Jan. 3, 2018, including English translation, 13 pages.

(Continued)

*Primary Examiner* — Charles G Freay
(74) *Attorney, Agent, or Firm* — RatnerPrestia

(57) ABSTRACT

A peristaltic pump for an apparatus for extracorporeal blood treatment, especially for a dialysis machine, for conveying fluid in the apparatus is disclosed. The peristaltic pump includes a rotor driven by a drive shaft, the rotor interacting with an elastically deformable fluid line so as to form a cross-sectional constriction which is displaced along the fluid line for conveying fluid by rotation of the rotor, wherein the rotor is coupled to the drive shaft by a coupling structure so as to transmit a torque, wherein the coupling structure couples the rotor and the drive shaft with a play in the direction of rotation relative to each other.

14 Claims, 5 Drawing Sheets

(56) References Cited

U.S. PATENT DOCUMENTS

| | | | |
|---|---|---|---|
| 5,657,000 A | 8/1997 | Ellingboe | |
| 6,041,709 A | 3/2000 | Wells et al. | |
| 6,648,619 B2* | 11/2003 | Otto | F01C 21/08 |
| | | | 418/152 |
| 7,625,189 B2 | 12/2009 | Cheng | |
| 8,500,564 B2* | 8/2013 | Shibahiraki | B62D 1/16 |
| | | | 403/359.1 |
| 9,334,903 B2* | 5/2016 | Nakagawa | F16D 3/50 |
| 9,562,529 B2 | 2/2017 | Schaefer | |
| 2005/0238515 A1 | 10/2005 | Kent | |
| 2005/0238516 A1 | 10/2005 | Kent | |
| 2007/0148022 A1 | 6/2007 | Cheng | |
| 2015/0252800 A1 | 9/2015 | Buckberry et al. | |
| 2018/0245578 A1* | 8/2018 | Winking | F04B 43/1253 |

FOREIGN PATENT DOCUMENTS

| | | |
|---|---|---|
| DE | 69605855 T2 | 5/2000 |
| JP | 2015532383 A | 11/2015 |
| WO | 9728368 A2 | 8/1997 |

OTHER PUBLICATIONS www.wikipedia.de, "Spiel (Technik)" Version of Dec. 25, 2014 with English Translation—4 Pages.

German Search Report for German Application No. 10 2016 114 959.4, with English translation, dated Feb. 27, 2017—15 Pages.

Chinese Office Action for Chinese Application No. 201710684648.9, dated Sep. 2, 2019 with translation, 10 pages.

Japanese Office Action for Japanese Application No. 2017-152943, dated Oct. 29, 2019, with translation, 4 pages.

* cited by examiner

PERISTALTIC PUMP HAVING ROTATORY PLAY

CROSS REFERENCE TO RELATED APPLICATIONS

This application claims priority to German application DE 10 2016 114 959.4 filed Aug. 11, 2016, the contents of such application being incorporated by reference herein.

FIELD OF THE INVENTION

The invention relates to a peristaltic pump for an apparatus for extracorporeal blood treatment, especially for a dialysis machine, for conveying fluid in the apparatus, the peristaltic pump including a rotor being driven to rotate by a drive shaft which interacts with an elastically/flexibly deformable fluid line to form a cross-sectional constriction, wherein the cross-sectional constriction is displaced (moved) along the fluid line by rotation of the rotor for conveying fluid and wherein the rotor is coupled to the drive shaft with a coupling structure so as to transmit a torque. Furthermore, the invention relates to an apparatus for extracorporeal blood treatment comprising a peristaltic pump according to aspects of the invention, especially a dialysis machine, comprising said peristaltic pump.

BACKGROUND OF THE INVENTION

In an apparatus for extracorporeal blood treatment, for example in a dialysis machine, it is the function of a peristaltic pump to convey a defined volume of a medium, such as blood or dialysis solution, by deforming and pinching off an elastically deformable fluid line from a negative pressure side (low-pressure side) to a positive pressure side (high-pressure side). Known peristaltic pumps in said medical apparatuses usually comprise a rotor, a pump casing and the elastic tube line disposed between the rotor and the pump casing as a fluid line. The rotor is coupled to a drive axle of the machine with a fixed torque, is driven by said drive axis and supports pressing elements, e.g. in the form of pressing rollers, adapted to be positioned in the radial direction and being biased against the tube line and the pump casing by compression springs.

DESCRIPTION OF THE RELATED ART

Such pump in which pressing rollers are biased radially outwardly with leaf springs is known, for example, from U.S. Pat. No. 3,737,256. In this pump, the rotor is connected to a drive axle via a coupling mechanism and is secured to the same in the axial direction with a screw. A drawback of this pump resides in the fact that the rotor can be released/replaced with the aid of a screwing tool only and with corresponding expenditure of time.

From WO 97/28368 A2 a peristaltic pump for a dialysis machine is known in which pressing rollers of a rotor biased radially outwardly with spiral springs interact with a pinch line. The rotor has a central receiving opening for a drive shaft of a drive motor and is coupled on the same with a pivoting handle which positively interacts with the drive shaft. The handle can be pivoted, on the one hand, into a coupling position in which it positively interacts with the drive shaft and, on the other hand, into an actuating position in which it is uncoupled from the drive shaft and forms a kind of crank for manual actuation of the rotor.

From U.S. Pat. No. 4,527,323 a peristaltic pump for a dialysis machine is known the rotor of which is configured similarly to that of U.S. Pat. No. 3,737,256 and with a journal is axially pushed into a slit of a drive axle so as to couple the rotor to the drive axle. The patent further discloses a handle adapted to be attached to the rotor for manual mounting or actuation of the rotor.

In known systems and especially in the afore-described pumps it is a general drawback that an increased stress of the drive components and thus increased wear may occur for pumps, when load changes or even load reversals occur during operation. This may especially be the case when the rotor is releasably connected or connectable to a drive axle, for example with radial form closure or force closure. Load changes or load reversals of this type may occur due to application and may result in varying or even changing strain of components of the drive, for example by load or torque reversal. A by-product of such load variations may be an increased noise emission.

In particular, such load variations may occur in peristaltic tube pumps in which, due to construction, there are always a run-in area and a run-out area which are generally referred to as run-in geometry and run-out geometry. The run-in area and the run-out area are due to the fact that the inserted tube system of the extracorporeal blood circulation has an open pump tube segment and it is not a fully closed tube segment. Therefore, the rotor is in engagement with the tube segment only via a particular angular range and pinches said tube segment in interaction with the pump casing, while in a remaining angular range outside the engagement it is released from the tube segment. Between the two angular ranges there is located the run-in portion in which the rotor engages in the tube segment and, respectively, the run-out portion in which the rotor disengages from the tube segment. When the rotor runs out of the run-out geometry, a short torque variation or even a torque reversal occurs, as the compression spring of the rotor required for compressing the pump segment/tube segment exploits the radial play newly formed during run-out for decompression and allows the rotor to advance relative to the rotation of the drive shaft (in addition to the speed thereof) until the drive shaft has caught up with the play again. Due to tolerances between the drive shaft and the coupling structure of the rotor interacting with the former, undesired detrimental transmissions of load on tooth flanks of the gear unit and disadvantageous and undesired acoustic effects may occur in this way.

SUMMARY OF THE INVENTION

Starting from the afore-described state of the art, an object underlying the present invention is to eliminate the afore-listed drawbacks, especially to provide a peristaltic pump for an apparatus for extracorporeal blood treatment, especially for a dialysis machine, which exhibits higher wear resistance and lower noise strain.

In accordance with the present invention, this object is achieved by a peristaltic pump for an apparatus for extracorporeal blood treatment, especially for a dialysis machine, for conveying fluid in the apparatus, wherein the peristaltic pump includes a rotor driven to rotate by a drive axle or drive shaft which interacts with an elastically/flexibly deformable fluid line to form a cross-sectional constriction which is moved along the fluid line for conveying fluid by rotation of the rotor, the rotor being coupled to the drive shaft or drive axle with a coupling structure (coupling) so as to transmit a torque, wherein the coupling structure couples the rotor and the drive shaft having a play in the direction of rotation toward each other.

Moreover, an object is achieved by an apparatus for extracorporeal blood treatment by a peristaltic pump according to aspects of the invention, especially as disclosed in the present description or as claimed by the attached claims.

The present subject matter of the invention can also be defined so that the invention consists in an increase in the radial degrees of freedom of a radial locking element (as component of the coupling structure according to aspects of the invention), thus causing undesired negative load transmission to the drive shaft and tooth flanks of an upstream gear unit interacting therewith which is present in known pumps to be reduced/prevented. Furthermore, acoustic effects occurring in known pumps (clicking) which are caused by load variations/torque variations upon passing the run-in and/or run-out area can be reduced and an improved service life of the gearing can be achieved by the invention.

The coupling structure facilitates sort of "free-wheeling" within an angular range defined by the coupling structure due to its geometry. Said angular range may have been established especially empirically. The selected/empirically established angular range usually is dependent on the design and the material properties of the individual functional elements of the peristaltic pump such as (namely) the rotor and the drive shaft, as well as on correspondingly applied/defined operating parameters (e.g. speed of rotation). The play in the direction of rotation generated by the coupling structure may act, according to aspects of the invention, basically in the run-out area of the rotor from the pump segment and/or in the run-in area of the rotor into the pump segment and achieve its effect intended according to aspects of the invention, respectively.

As described in the foregoing with respect to the state of the art, in the run-in area and/or in the run-out area variation or even reversal of radial forces acting on pressure elements of the rotor (or of moments/circumferential forces acting on the rotor) may occur which might also affect the drive shaft and a drive train operatively connected to the latter (gearing). Upon run-out of the rotor, especially a pressing element interacting with the fluid line (fluid line supporting structure), from the portion pinching the fluid line, for example an additional torque may be caused especially in the direction of rotation. This would have to be absorbed and compensated by the drive shaft and thus would have a negative effect as regards acoustic emissions (clicking noise) and load of the drive shaft and the gearings thereof. The play of the coupling structure provided according to aspects of the invention may compensate for or at least reduce such variations by the fact that the rotor may have relative advance and relative overrun with respect to the drive shaft. Despite the provided play, the rotor and the drive shaft are coupled to each other so as to transmit a torque.

By the free-wheeling function according to aspects of the invention (due to the play of the coupling structure acting in the direction of rotation) especially also a two-sided direction of rotation (forward and backward) may be realized. Moreover, the rotor may be positioned to be largely free, which is required/advantageous for example within the scope of inserting and removing the fluid line, especially within the scope of an automatic threading and unthreading function of the fluid line. At the same time, undesired negative load transmissions to tooth flanks of a gearing operatively connected to the drive shaft or of a gear unit can even be completely eliminated. Acoustic impacts can be definitely reduced as compared to the state of the art. In total, the invention has a positive influence on the service life of the gearing. On principle, the invention is applicable to almost all known peristaltic pumps, no matter whether the rotor and the drive shaft are coupled to each other in a fixed or releasable manner. Moreover, it is applicable in the case of form closure, force closure as well as material closure between the rotor and the drive shaft.

The peristaltic pump of the apparatus according to aspects of the invention may convey a defined volume of a medium such as blood or dialysis solution in a common way from a low-pressure side, usually the arterial side, to a high-pressure side, usually the venous side. The elastic fluid line is inserted into the same formed between the rotor and the support surface formed by the support surface module in loop shape. It may be guided or retained especially by the casing module. The rotor and the supporting surface supporting the elastic fluid line are configured and adapted to each other so that a conveying distance is formed therebetween. In the course thereof, the elastically deformable fluid line is deformed and pinched off upon rotation of the rotor about the rotor shaft. The rotor is configured so that the fluid line is pinched only locally or in portions. For example, it may include pinch elements biased against the fluid line and/or adapted to be positioned relative to the rotor shaft. The pinching point caused by contact with the rotor moves along with the rotating rotor and is so-to-speak moved through the fluid line from the low-pressure side to the high-pressure side. As a consequence, fluid is forced out of the fluid line in the conveying direction. Resupplied fluid is sucked into the line by low pressure, especially vacuum, forming due to elastic re-formation of the fluid line after deformation by the rotor. The elastically deformable fluid line may be a tube, for example.

By the invention especially the following advantages can be achieved:

By the (angularly/peripherally limited) free-wheeling function in the form closure of the coupling structure the requirements to a two-sided direction of rotation can be maintained;

undesired negative load transmissions especially to the tooth flanks of an (upstream) gearing unit can be (completely) eliminated;

acoustic influences are (definitely) reduced by the integrated free-wheeling function;

the service life of the gearing can be positively influenced;

definitely quieter treatment of patients is possible;

less wear is detected at the gearing.

Advantageous embodiments of the invention are claimed in the subclaims and shall be illustrated hereinafter.

One embodiment of the peristaltic pump is wherein the rotor and the drive shaft are removably coupled to each other. This facilitates especially easy cleaning and maintenance of the pump. Moreover, the fluid line can be easily replaced.

Preferably, the coupling structure may have at least one flat first guiding contour formed in parallel to the axis of rotation. Said first guiding contour may be formed either on the rotor side or on the drive shaft side. It may be especially in the form of a guiding surface, for example in the form of a flat guiding surface. Such guiding surface can be configured especially simply by flattening the drive shaft just in parallel to the axis of rotation thereof, for example. It is of particular advantage when the coupling structure includes two flat first guiding contours parallel to each other on diametrically opposed sides of the axis of rotation. This allows for uniform torque transmission, especially in the case of alternating directions of rotation.

According to another embodiment of the invention, the coupling structure includes at least a second guiding contour. It is formed and intended for interaction with the first guiding contour of the coupling structure. It may be formed especially of at least two guiding surfaces being arranged in parallel to the axis of rotation and inclined relative to each other. Also the second guiding contour may be provided on the drive shaft side or on the rotor side. When the first guiding contour is formed on the rotor side, for example, the second guiding contour is formed on the drive shaft side and vice versa. The first and second guiding contours cause the transmission of the torque between the drive shaft and the rotor.

According to a further embodiment of the invention, the second guiding contour may be rounded in the transition between the two guiding surfaces thereof. Alternatively, the first guiding contour may be rounded in this way. The radius of such rounding may range from about 5 mm to about 25 mm, more preferred from about 10 mm to about 20 mm, even more preferred about 15 mm. Such rounded geometry facilitates an especially smooth transition between the advance and the overrun in the case of load change in the area of the play provided by the coupling structure. The first guiding contour may so-to-speak roll off the radius of the second guiding contour during relative rotation within the play range and may smoothly change from a first relative position (e.g. synchronous run) to a second relative position (e.g. advance). As a result, this permits smooth re-engagement of the drive shaft in a torque closure with the coupling structure and thus with the rotor. It is of special advantage when the coupling structure according to an embodiment of the invention includes two second guiding contours of this type on diametrically opposed sides of the axis of rotation.

A similar effect and advantages may be achieved by the second guiding contour being configured to be rounded in portions or else completely. The rounding extends especially in parallel to the axis of rotation. Its radius may preferably be within a range of from 5 mm to about 25 mm, more preferred from about 10 mm to about 20 mm or even more preferred about 15 mm. It is of particular advantage when the coupling structure according to an embodiment of the invention includes two second guiding contours of this type on diametrically opposed sides of the axis of rotation.

The first and second guiding contour(s) may be configured especially simply in that, according to a further embodiment of the invention, the drive shaft or the rotor has a central groove or is flattened on both sides. This is robust, easy to manufacture and may especially easily allow for dismounting the rotor from the drive shaft.

One embodiment of the invention is wherein the rotor can be coupled to the drive shaft with a locking element or includes the locking element, wherein the first guiding contour or the second guiding contour (and, respectively the first guiding contours or the second guiding contours) are formed on the locking element. The latch element may serve, on the one hand, for forming a torque closure between the rotor and the drive shaft. On the other hand, it may serve for locking the rotor in a condition positioned on the drive shaft so that inadvertent release of the rotor during treatment can be excluded.

The locking element may especially be arranged about a pivot axis transversely to the axis of rotation to be pivotal on the rotor. It may be adapted to be positioned into a locking position coupling the rotor and the drive shaft via the coupling structure to each other and into an unlocking position uncoupling the rotor from the drive shaft. For a pump including such quick acting lock element it is advantageous that the rotor can be manually released/replaced with little expenditure of time without the aid of a tool/screwing tool. The locking element may interact with the rotor especially in the unlocking position such that it may be used as a handle for manual actuation and for manual drive of the rotor, respectively. This is especially advantageous in the case of power breakdowns to be able to ensure continuous pump function. In the unlocking position, the rotor may be uncoupled from the drive shaft so that, for example, the fluid line may be replaced and/or the pump is easily accessible for cleaning.

It can also be stated that the invention relates to a functionally integrated locking element of a releasable positive-locking shaft-hub connection of a rotor to a drive shaft for the rotor. The rotor and, where necessary, the drive shaft may be components of a peristaltic roller pump, especially a tube pump for medical engineering the intended application of which may be found especially in extracorporeal blood treatment. The rotor allows, together with the elastic material properties of the pump segment which is inserted against a cylindrical running surface of the pump casing in loop shape, a pumping function that ensures blood delivery to a dialyzer.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
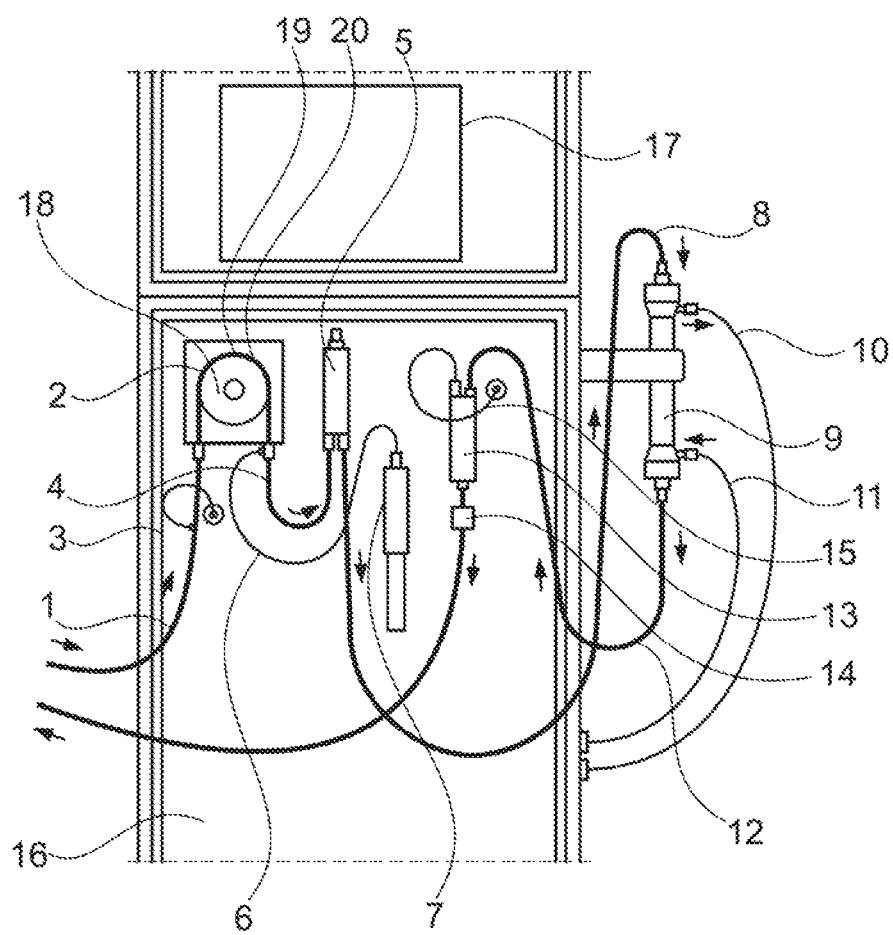
FIG. 1 shows a schematic representation of a cutout of an apparatus for extracorporeal blood treatment.

FIG. 1 exemplifies a cutout of an apparatus for extracorporeal blood treatment according to aspects of the invention. There is substantially shown the entire extracorporeal blood circulation of the apparatus. It includes an arterial blood line 1 with which blood is guided from a patient (not shown) to a peristaltic pump 2 of modular design of the treatment apparatus. Upstream of the peristaltic pump 2 an arterial pressure sensor 3 is provided by which the pressure upstream of the peristaltic pump 2, i.e. the low-pressure side pressure is measured. On the high-pressure side of the peristaltic pump 2 a high-pressure blood line 4 leads to an arterial blood collector 5. Directly at the outlet of the peristaltic pump 2, additive may be supplied with a feed line 6 and a pump 7 to the blood present in the system, e.g. heparin for hemodilution.

From the arterial blood collector 5 a line 8 guides blood which is under high pressure but is untreated yet and loaded with waste materials to a dialyzer 9. On the inlet side, dialysis solution is supplied thereto via a dialysis solution feed line 10. In the dialyzer 9 blood is treated, e.g. purified in a known manner with the dialysis solution. Used dialysis solution is removed from the dialyzer 9 via a dialysis solution drain 11 and is supplied to waste disposal or recycling (not shown). Treated blood is guided with blood drain 12 from the dialyzer 9 to a venous air collector 13 where air is separated with an air trap 14. At the venous air collector 13 a venous pressure sensor 15 is provided by which the venous pressure, namely the high-pressure side pressure, is detected. Treated blood is returned from the air trap 14 via a venous blood line 16 to the patient. In FIG. 1 also a unit 17 for monitoring and controlling the apparatus is shown. The apparatus for extracorporeal blood treatment is encapsulated by a housing 100 which is configured at least in part as a formed sheet metal part.

The peristaltic pump 2 includes a rotor 18 indicated in FIG. 1 and an equally indicated pump casing 19 having a guiding surface. Between the rotor 18 and the guiding surface of the pump casing 19 an elastically deformable fluid line 20 is arranged which is connected, on the inlet side, to the arterial blood line 1 and, on the outlet side, to the high-pressure blood line 4. The fluid line 20 is deformed and pinched by the effect of the rotor 18 between the same and the guiding surface of the pump casing 19 so that fluid delivery from the arterial blood line 1 to the high-pressure blood line 4 is brought about.

Figure 2:
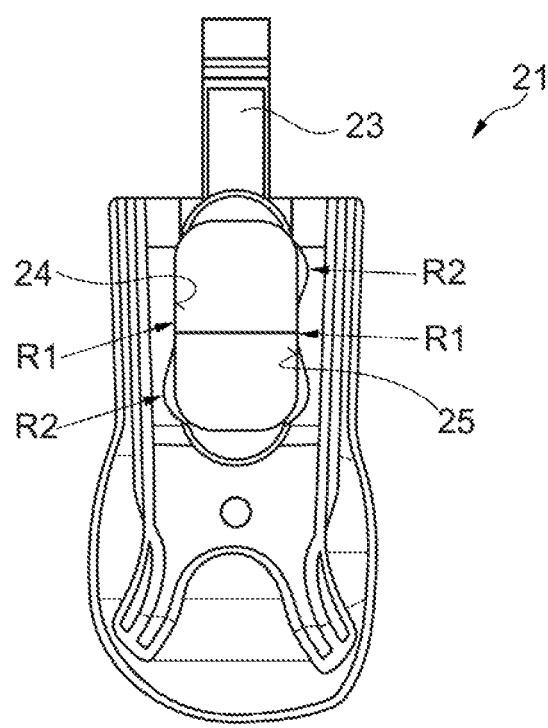
FIG. 2 shows a top view onto a locking element comprising a coupling structure according to aspects of the invention.

FIG. 2 illustrates a locking element 21 for locking the rotor 18 on a drive shaft 22 of the dialysis machine visible in the FIGS. 4 to 7. The locking element 21 includes a pivoted tab 23 by which it can be pivotally fixed to the rotor 18. A recess whose walls are forming respective second guide contours 24, 25 in accordance with the invention is configured in the locking element 21.

Figure 3:
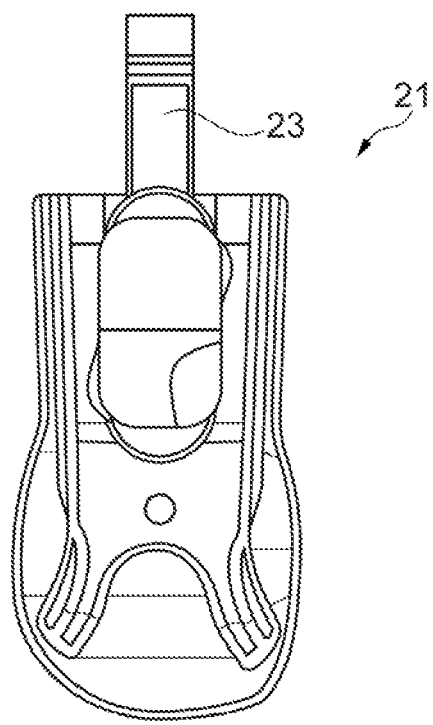
FIG. 3 shows another top view onto the locking element of FIG. 2.
Figure 5:
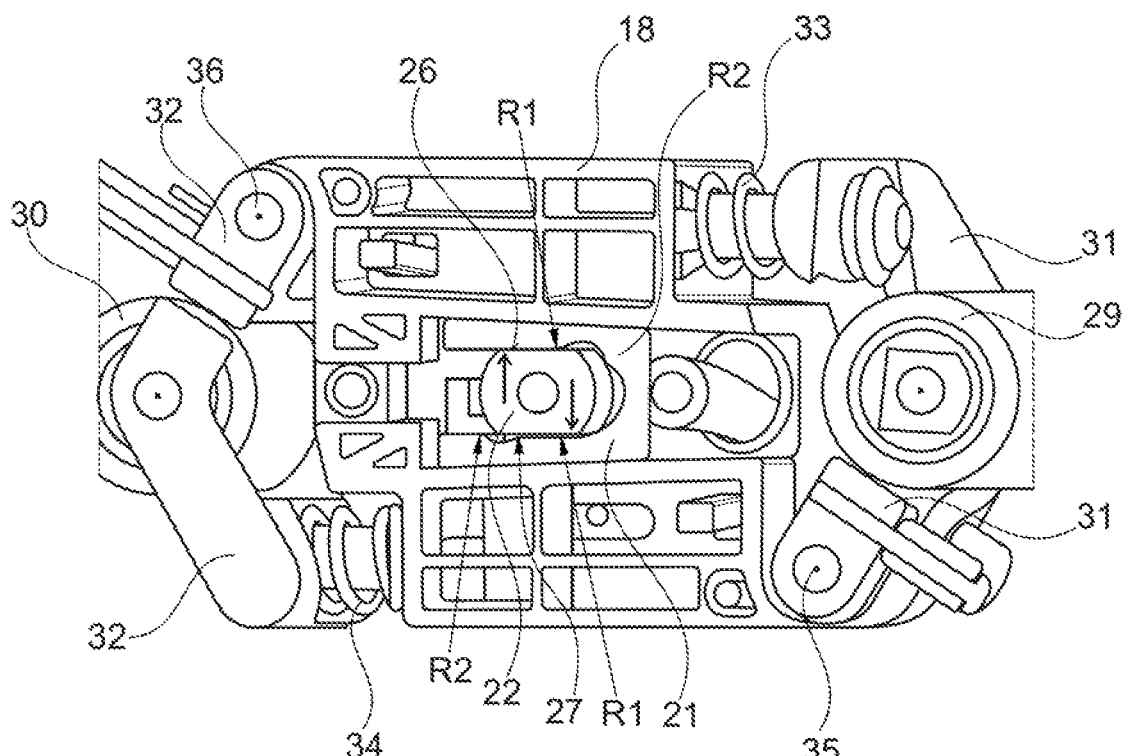
FIG. 5 shows a bottom view of a rotor comprising a coupling structure according to aspects of the invention in a first operating condition.
Figure 6:
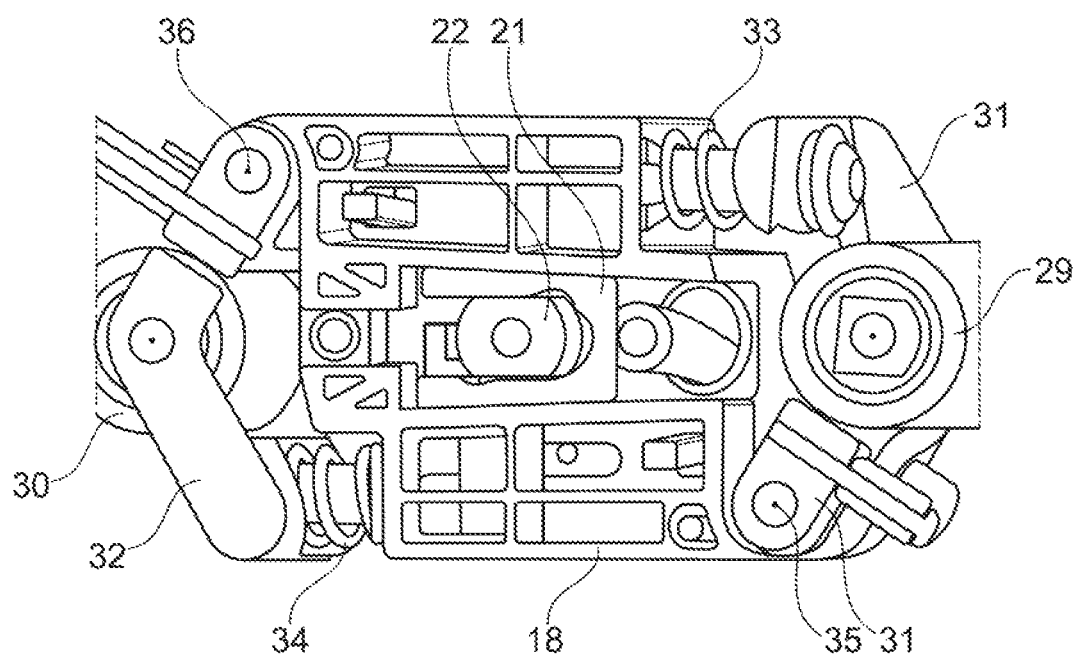
FIG. 6 shows a bottom view of the rotor in a second operating condition.
Figure 7:
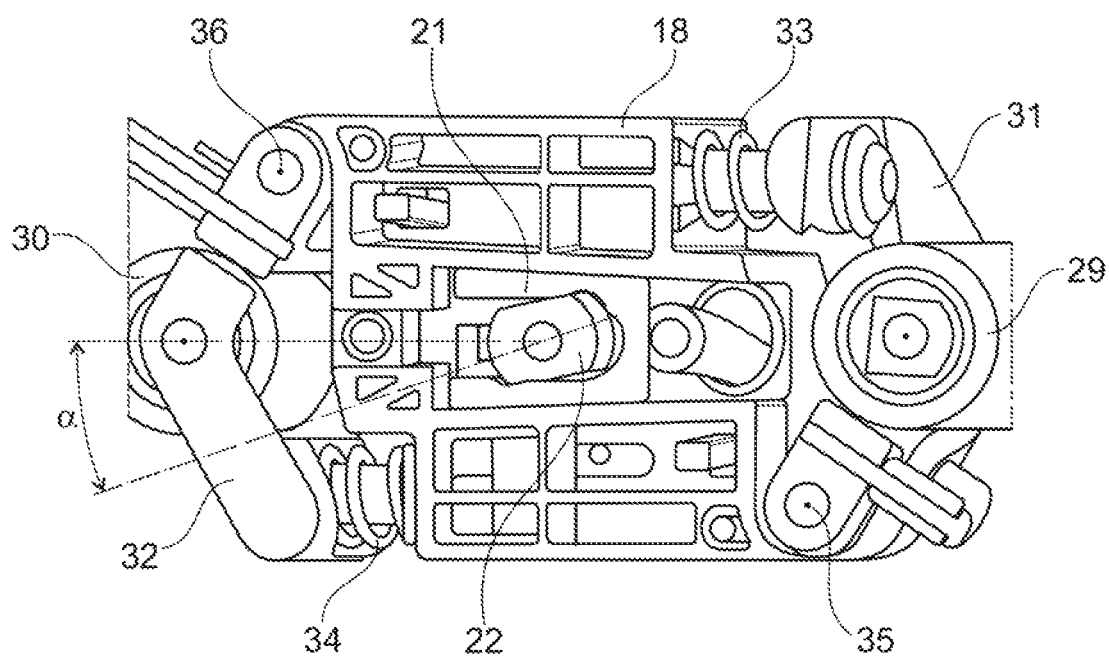
FIG. 7 shows a bottom view of the rotor in a third operating condition.
Figure 8:
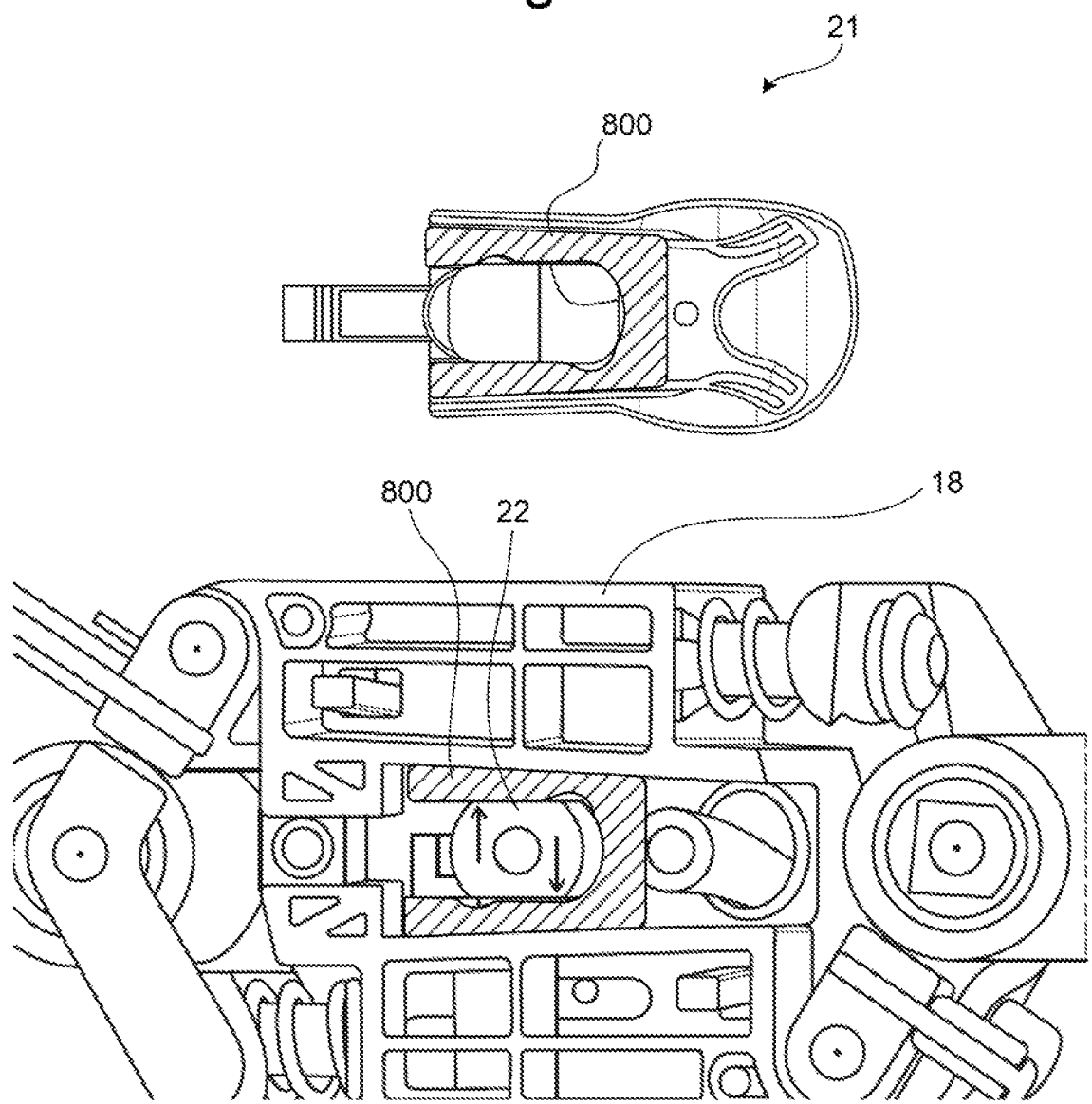
FIG. 8 illustrates an example of how the rotor engages the drive shaft by way of the intervening locking element structure.

The FIGS. 5 to 7 illustrate the second guiding contours 24, 25 of the locking element 21 in mesh with the drive shaft 22. The latter is configured to be flattened on both sides in parallel with its axis of rotation and includes two first guiding contours in the form of flattened portions or guiding planes 26, 27 which are diametrically opposed to each other. Said guiding planes 26, 27 are flat and configured in parallel to each other. In contrast to this, the guiding contours 24, 25 of the first guiding contour are configured to be rounded having a first radius R1 and a second radius R2. According to aspects of the invention, the first radius may be from about 5 mm to about 25 mm, more preferred about from 10 mm to about 20 mm, even more preferred about 15 mm. The second radius preferably is about 3 mm. In FIGS. 5 to 7 furthermore pressing rollers 29, 30 of the rotor 18 are illustrated which interact with the fluid line 20 and pinch the same for conveying fluid therethrough. Each of the pressing rollers 29, 30 is rotatably supported on a corresponding pivoted arm 31 and 32, respectively, being biased by a compression spring 33, 34 so as to contact the fluid line 20. Each of the pivoted arms 31, 32 is pivoting about a pivot axis 35, 36. FIG. 8 illustrates how a portion 800 of the locking element of FIG. 3 fits in the rotor 18 to engage the drive shaft 22.

Unless either of the pressing rollers 29, 30 is in pinching engagement with the fluid line 20, the pivoted arm 31 and 32, respectively, thereof is pivoted outwards, i.e. away from the drive shaft 22, by the action of the respective compression spring 33, 34. In the run-in area the respective pressing roller 29, 30 enters into contact with the fluid line 20 and, due to the distance between the pressing roller 29, 30 from the supporting surface decreasing during continuous rotation, is pivoted inwards in the direction of the drive shaft 22. After passing the run-in portion the respective pressing roller 29, 30 is provided in the conveying portion of the fluid line 20 and pinches the same so as to convey fluid. After passing the conveying portion the respective pressing roller 29, 30 enters into the run-out portion and, when passing the same, the radial distance of the pressing roller 29, 30 from the guiding surface increases again and the corresponding pivoted arm 31, 32 pivots outward again (away from the drive shaft 22) due to the decreasing pressure exerted by the fluid line 20. The maximum relative pivot angle α between the rotor 18 and the drive shaft 22 given with maximum advance is inserted in FIG. 7.

Figure 4:
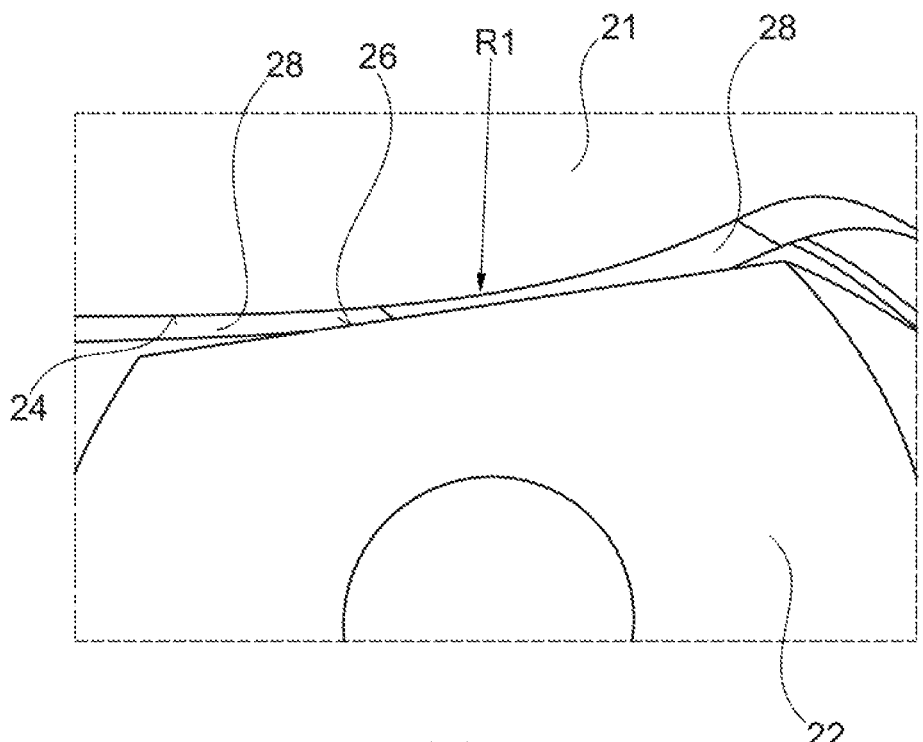
FIG. 4 shows an enlarged cutout of a coupling structure according to aspects of the invention.

FIG. 4 illustrates in a magnification that between the rounded guiding contours 24, 25 of the second guiding contour and the flat guiding surfaces of the first guiding contour a gap 28 providing play in the direction of rotation is formed. It can be clearly inferred that the first guiding contour 26, 27 may roll off the second guiding contours 24, 25 upon rotation of the rotor 18 relative to the drive shaft 22. Said roll-off process or the relative rotation between the rotor 18 and the drive shaft 22 becomes especially clear from a comparison of FIGS. 5, 6 and 7. In FIG. 5, an operating condition is shown in which the drive shaft 22 is in mesh with the rotor 18 in an operating position or a neutral position. Such position is given when none of the two pressing rollers 29, 30 is provided in the run-in area or in the run-out area. If either of the rollers 29, 30 is provided in the area of the pump outlet (where the roller lifts off the fluid line), the rotor 18 is accelerated by the pressure of the respective compression spring 33, 34 in the direction of rotation (clockwise in the Figures) and therefore temporarily rotates more quickly than the driven shaft 22. This condition (advance) is illustrated in FIGS. 6 and 7. Due to the play 28, the afore-described relative positioning between the rotor 18 and the drive shaft 22 and, consequently, the described variations of loads and moments are not transmitted to the latter.

The invention claimed is:

1. A peristaltic pump of an apparatus for extracorporeal blood treatment, the peristaltic pump configured to convey fluid in the apparatus, the peristaltic pump comprising:
  a drive shaft;
  a rotor driven by the drive shaft, the rotor configured to press an elastically deformable fluid line against a guiding surface of a pump casing so as to form a cross-sectional constriction, wherein said cross-sectional constriction is displaced along the fluid line to convey fluid by rotation of the rotor, and the pump casing extends partially around a rotation path of the rotor between a run-in portion in which the rotor engages the elastically deformable fluid line, and a run-out portion in which the rotor disengages the elastically deformable fluid line; and
  a coupling structure coupling the rotor to the drive shaft so as to transmit a torque, the coupling structure coupling the rotor and the drive shaft with play between the coupling structure and the drive shaft in the direction of rotation.

2. The peristaltic pump according to claim 1, wherein the rotor and the drive shaft are releasably coupled to each other.

3. The peristaltic pump according to claim 1, wherein the coupling structure includes at least one flat first guiding contour formed parallel to an axis of rotation.

4. The peristaltic pump according to claim 3, wherein the coupling structure further includes two flat first guiding contours parallel to each other on diametrically opposed sides of the axis of rotation.

5. The peristaltic pump according to claim 1, wherein the coupling structure includes at least a second guiding contour including at least two guiding surfaces which are arranged in parallel to an axis of rotation and inclined relative to each other.

6. The peristaltic pump according to claim 5, wherein the second guiding contour is at least partially rounded.

7. The peristaltic pump according to claim 6, wherein the second guiding contour has a radius of 5 mm to 25 mm.

8. The peristaltic pump according to claim 7, wherein the second guiding contour has a radius of 10 mm to 20 mm.

9. The peristaltic pump according to claim 8, wherein the second guiding contour has a radius of 15 mm.

10. The peristaltic pump according to claim 5, wherein the coupling structure includes two second guiding contours on diametrically opposed sides of the axis of rotation, each second guiding contour including at least two guiding surfaces which are arranged in parallel to the axis of rotation and inclined relative to each other.

11. The peristaltic pump according to claim 2, wherein the drive shaft or the rotor has a central groove or flattened portions on two sides.

12. The peristaltic pump according to claim 1, wherein the coupling structure comprises a locking element that is movable relative to the rotor.

13. The peristaltic pump according to claim 1, wherein the locking element is adapted to be positioned into a locking position coupling the rotor to the drive shaft via the coupling structure and into an unlocking position uncoupling the rotor from the drive shaft.

14. The peristaltic pump according to claim 1, wherein the apparatus is a dialysis machine.

* * * * *